United States Patent
Qu et al.

(10) Patent No.: US 11,345,746 B2
(45) Date of Patent: May 31, 2022

(54) FULLY HUMAN ANTIBODY SPECIFICALLY INHIBITING CONNEXIN 26

(71) Applicant: SHANGHAITECH UNIVERSITY, Shanghai (CN)

(72) Inventors: Zhihu Qu, Shanghai (CN); Guang Yang, Shanghai (CN); Fabio Mammano, Padua (IT); Francesco Zonta, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 544 days.

(21) Appl. No.: 15/781,463

(22) PCT Filed: Dec. 14, 2016

(86) PCT No.: PCT/CN2016/109847
§ 371 (c)(1),
(2) Date: Jun. 4, 2018

(87) PCT Pub. No.: WO2017/128880
PCT Pub. Date: Aug. 3, 2017

(65) Prior Publication Data
US 2020/0299366 A1   Sep. 24, 2020

(30) Foreign Application Priority Data
Jan. 27, 2016   (CN) .......................... 201610056295.3

(51) Int. Cl.
*C07K 16/18*   (2006.01)
*A61K 39/395*   (2006.01)
*A61K 39/00*   (2006.01)

(52) U.S. Cl.
CPC ........ *C07K 16/18* (2013.01); *A61K 2039/505* (2013.01); *C07K 2317/21* (2013.01); *C07K 2317/51* (2013.01); *C07K 2317/524* (2013.01); *C07K 2317/526* (2013.01); *C07K 2317/55* (2013.01); *C07K 2317/565* (2013.01); *C07K 2317/622* (2013.01); *C07K 2317/76* (2013.01)

(58) Field of Classification Search
None
See application file for complete search history.

(56) References Cited

FOREIGN PATENT DOCUMENTS

| CN | 102099475 A | 6/2011 |
| CN | 102105492 A | 6/2011 |
| CN | 105566495 A | 5/2016 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
GenPept accession No. 2GHW_B, NCBI, 2012. amino acid sequence part.
Wang Yafe, et al., Expression of Connexin26 in Mouse Cochlea Lateral Wall after Noise Exposure, Journal of Audiology and Speech Pathology, 2013, pp. 263-266, vol. 21.
Yun Hoon Choung, et al., Functional Study of GJB2 in Hereditary Hearing Loss, The Laryngoscope, Sep. 2002, pp. 1667-1671, vol. 112.
Eva Thonnissen et al., Human connexin26 (GJB2) deafness mutations affect the function of gap junction channels at different levels of protein expression, Jun. 2002, pp. 190-197, vol. 111.
Daniel A. Goodenough et al., Gap Junctions, Cold Spring Harbor Perspectives in Biology, 2009, pp. 1-19, Cold Spring Harbor Laboratory Press.
Andrew L. Harris, Connexin Channel Permeability to Cytoplasmic Molecules, Prog Biophys Mol Biol. , 2007, pp. 120-143, 94(1-2).
Goran Sohl et al., Gap junctions and the connexin protein family, Cardiovascular Research, 2004, pp. 228-232, vol. 62, Elsevier.
Chih-Jen Wei et al., Connexins and Cell Signaling in Development and Disease, Annu. Rev. Cell Dev. Biol., 2004, pp. 811-838, vol. 20.
Andrei B. Belousov et al., Neuronal gap junctions: making and breaking connections during development and injury, Trends Neurosci., Apr. 2013, pp. 227-236, 36(4).
Ilaria Fasciani et al., Regulation of connexin hemichannel activity by membrane potential and the extracellular calcium in health and disease, Neuropharmacology, 2013, pp. 479-490, vol. 75, Elsevier.
Dale W. Laird, Life cycle of connexins in health and disease, Biochem. J., 2006, pp. 527-543, vol. 394, Great Britain.
Radoslaw Dobrowolski et al., Connexin-Caused Genetic Diseases and Corresponding Mouse Models, Antioxidants & Redox Signaling, 2009, pp. 283-295, vol. 11, No. 2.

(Continued)

*Primary Examiner* — Joanne Hama
*Assistant Examiner* — Jon M Lockard
(74) *Attorney, Agent, or Firm* — Foley & Lardner LLP

(57) ABSTRACT

The present invention provides a fully human antibody specifically inhibiting Connexin 26, characterized in that it is a recombinant immunoglobulin having the structure of scFv-Fc, wherein scFv refers to a single-chain antibody comprising a heavy chain variable region and a light chain variable region, the amino acid sequence of the heavy chain variable region is SEQ ID NO: 1, the amino acid sequence of the light chain variable region is SEQ ID NO: 2, and Fc refers to constant region. The present invention uses the first 41-56 amino acid sequence of extracellular region of Connexin26 as an antigen, the sequence thereof is KEVWGDEQADFVCNTL. Through the biochemical analysis and immunofluorescence identification of the antibody obtained by single-chain antibody phage display library and screening technology, it was confirmed that the antibody provided by the present invention could specifically recognize Connexin 26 and inhibit its hemichannel activity. Animal experiments show that this antibody significantly inhibits the hemichannel activity of mouse cochlear tissue sections. Therefore, the antibody can be used in the treatment of Connexin mutation associated diseases.

10 Claims, 5 Drawing Sheets
Specification includes a Sequence Listing.

(56) References Cited

OTHER PUBLICATIONS

Federico Ceriani et al., A rapid and sensitive assay of intercellular coupling by voltage imaging of gap junction networks, Ceriani and Mammano Cell Communication and Signaling, 2013, pp. 1-11, 11:78.
Francisco J. Del Castillo et al., The DFNB1 subtype of autosomal recessive non-syndromic hearing impairment, Frontiers in Bioscience 16, Jun. 2011, pp. 3252-3274.
Leopoldo Zelante et al., Connexin26 mutations associated with the most common form of non-syndromic neurosensory autosomal recessive deafness (DFNB1) in Mediterraneans, Human Molecular Genetics, 1997, pp. 1605-1609, vol. 6, No. 9, Oxford University Press.
Martine Cohen-Salmon et al., Connexins Responsible for Hereditary Deafness—The Tale Unfolds, Gap Junctions in Development and Disease, 2005, pp. 111-134.
Michel Leibovici et al., Mouse Models for Human Hereditary Deafness, Current Topics in Developmental Biology, 2008, pp. 385-429, vol. 84.

\* cited by examiner

FULLY HUMAN ANTIBODY SPECIFICALLY INHIBITING CONNEXIN 26

CROSS REFERENCE TO THE RELATED APPLICATIONS

This application is the national phase entry of International Application No. PCT/CN2016/109847, filed on Dec. 14, 2016, which is based upon and claims priority to Chinese Patent Application No. 201610056295.3, filed on Jan. 27, 2016, the entire contents of which are incorporated herein by reference.

REFERENCE TO A "SEQUENCE LISTING"

An ASCII text file of Sequence Listing is submitted separately, naming "GBSH006-POA-Sequence Listing-20200917", created on Sep. 17, 2020, and sized 10,061 bytes, and the ASCII text file is incorporated herein by reference.

TECHNICAL FIELD

The present invention belongs to the field of biotechnology medicine, in particular the present invention provides the single-chain antibody or plasmid expressing the antibody, which is capable of specifically recognizing Connexin 26 expressed in human cochlea and skin tissue and inhibiting hemichannels of Connexin 26, and the use of antibody in the preparation of a medicament and a diagnostic kit for treating deafness, skin disease and tumor caused by Connexin 26 mutation. The present invention also provides the diagnostic kit prepared by using the antibody. The kit comprises the monoclonal antibody as an active ingredient.

BACKGROUND

Gap junction is a cell-cell junction formed by ion channels. Gap junction channels connect the cell-cell cytoplasm, allowing smaller molecules smaller than 1.8 KD to pass freely, such as ions, metabolites and second messengers[1,2]. In vertebrates, a gap junctional pathway composed of Connexin mediates the exchange of ions, small molecules, and signaling molecules between adjacent cells and are of high importance in the early stage of mammalian development. Gap junction channels can be composed by many different connexin proteins and display different permeability characteristics, which depend on the connexin composition. Adjacent cells use gap junction-mediated intercellular communication or gap-independent pathway to transmit developmental signals and regulate cell proliferation, migration and differentiation during development. Proteins of Connexin family are widely expressed in vertebrate cells. The hexamers of this family member are located on the cell membrane to form gap junctions or hemichannels and mediate the exchange of material between cells, and the extracellular matrix. The genes encoding connexin proteins in the genome make up the connexin gene family[3].

So far, 21 kinds of connexin genes have been found in human genome, and 20 kinds of the connexin gene[3] have been found in the mouse genome. Many important cell functions including cell growth regulation, differentiation and development is mediated by gap junction channels and connexin hemichannel communication[4-6]. Mutations in connexin genes are associated with many human diseases, including cardiovascular abnormalities, peripheral neuropathy, cataracts and deafness. Connexin 26 (Cx26) and Connexin 30 (Cx30) channels and hemichannels are involved in the potassium ions cycling of inner ear, and deletion of Cx26 and Cx30 causes profound hearing loss and concomitant cell death in developing organ of Corti in the cochlea [4,7,8]. $C_x26$ and Cx30 are expressed by two adjacent genes (GJB2 and GJB6), while Cx26 and Cx30 are connected with non-responsive cells in the inner ear to form polytopes. Both proteins are co-expressed in the inner ear[9]. DNFB1 is located on chromosome $13_811$-q12[10]. Fifty percent of hereditary deafness is related to DFNB1, with up to 79% in Mediterranean[10,11]. Deletion mutations at Cx26 and Cx30 have a profound effect on the organ formation of the cochlear spirals[12-14]. In some cases, point mutations in connexins can cause aberrant hemichannel opening or closing, which will result in deafness and skin diseases[15]. Antibodies that specifically recognize Cx26 and restore its function are expected to treat deafness and skin diseases caused by connexin mutations.

In recent years, monoclonal antibodies have been playing an important role in the diagnosis and treatment of diseases, especially for diseases that express specific antigens. The detection of the reaction of monoclonal antibodies and antigens can be used as the golden standard for disease diagnosis. Monoclonal antibodies also play an important role as drugs in autoimmune diseases and tumor diseases.

Diseases caused by connexin mutations have relatively low incidences and relatively few treatment drugs. Moreover, no antibody drug targeting connexin channels is available to treat deafness or skin diseases due to difficulties in the administration of antibody drugs. There are no kits for clinical diagnosis, so the single chain antibodies capable of recognizing and binding connexin will be an important tool in the diagnosis and treatment of colorectal cancer.

REFERENCES

1. D. A. Goodenough, D. L. Paul, Gap junctions, Cold Spring Harb Perspect Biol 1 (2009) a002576.
2. A. L. Harris, Connexin channel permeability to cytoplasmic molecules, Prog Biophys Mol Biol 94 (2007) 120-143.
3. G. Sohl, K. Willecke, Gap junctions and the connexin protein family, Cardiovasc Res 62 (2004) 228-232.
4. C. J. Wei, X. Xu, C. W. Lo, Connexins and cell signaling in development and disease, Annu Rev Cell Dev Biol 20 (2004) 811-838.
5. A. B. Belousov, J. D. Fontes, Neuronal gap junctions: making and breaking connections during development and injury, Trends in Neurosciences 36 (2013) 227-236.
6. I. Fasciani, A. Temperan, L. F. Perez-Atencio, A. Escudero, P. Martinez-Montero, J. Molano, J. M. Gomez-Hernandez, C. L. Paino, D. Gonzalez-Nieto, L. C. Barrio, Regulation of connexin hemichannel activity by membrane potential and the extracellular calcium in health and disease, Neuropharmacology (2013).
7. D. W. Laird, Life cycle of connexins in health and disease, Biochem J 394 (2006) 527-543.
8. R. Dobrowolski, K. Willecke, Connexin-caused genetic diseases and corresponding mouse models, Antioxid Redox Signal 11 (2009) 283-295.
9. F. Ceriani, F. Mammano, A rapid and sensitive assay of intercellular coupling by voltage imaging of gap junction networks, Cell Commun Signal 11 (2013) 78.
10. F. J. del Castillo, I. del Castillo, The DFNB1 subtype of autosomal recessive non-syndromic hearing impairment, Front Biosci 16 (2011) 3252-3274.

11. L. Zelante, P. Gasparini, X. Estivill, S. Melchionda, L. D'Agruma, N. Govea, M. Mila, M. D. Monica, J. Lutfi, M. Shohat, E. Mansfield, K. Delgrosso, E. Rappaport, S. Surrey, P Fortina, Connexin26 mutations associated with the most common form of non-syndromic neurosensory autosomal recessive deafness (DFNB1) in Mediterraneans, Hum Mol Genet 6 (1997) 1605-1609.
12. M. Cohen-Salmon, F. J. del Castillo, C. Petit, Connexins Responsible for Hereditary Deafness—The Tale Unfolds, in: E. Winterhager (Ed.), Gap Junctions in Development and Disease, Springer-Verlag, Berlin, 2005, pp. 111-134.
13. M. Leibovici, S. Safieddine, C. Petit, Mouse models for human hereditary deafness, Curr Top Dev Biol 84 (2008) 385-429.
14. R. Dobrowolski, K. Willecke, Connexin-Caused Genetic Diseases and Corresponding Mouse Models, Antioxidants & Redox Signaling 11 (2009) 283-295.
15. F. J. del Castillo, I. del Castillo, The DFNB1 subtype of autosomal recessive non-syndromic hearing impairment, Frontiers in Bioscience-Landmark 16 (2011) 3252-3274.

SUMMARY

An object of the present invention is to provide a single chain antibody, which specially binds to human Connexin 26 antigen and thus can be used in the preparation of medicaments treating diseases caused by mutations in Connexin 26 or diagnostic kits relevant to Connexin 26.

To achieve the above object, the present invention provides a fully human antibody specifically inhibiting Connexin 26, characterized in that it is a recombinant immunoglobulin having the structure of scFv-Fc, wherein scFv refers to a single-chain antibody comprising a heavy chain variable region and a light chain variable region, the amino acid sequence of the heavy chain variable region is SEQ ID NO: 1, the amino acid sequence of the light chain variable region is SEQ ID NO: 2, and Fc refers to a constant region.

Preferably, the constant region comprises a CH2 constant region and a CH3 constant region.

Preferably, the fully human antibody specifically inhibiting Connexin 26 specifically recognizes the 41-75 amino acid portion of the extracellular region of Connexin 26.

The present invention also provides a genetically engineered antibody, characterized in that it has 30% or more homologous sequences to a single chain antibody of the fully human antibody specifically inhibiting Connexin 26.

Preferably, the genetically engineered antibody comprises one of a Fab fragment, a F(ab)' fragment, an Fd fragment, an Fv fragment and an Fc fragment, a combination of two or more of the foregoing fragments, or a derivative of at least one of the foregoing fragments with other proteins or peptide chains.

Preferably, the heavy chain CDR 3 region sequence of the genetically engineered antibody is DFSWRGYYMDV (amino acids 99-109 of SEQ ID NO: 1), the light chain CDR3 region sequence is QQYGSSPRT (amino acids 89-97 of SEQ ID NO: 2).

The present invention also provides a nucleotide sequence encoding a fully human antibody specifically inhibiting Connexin 26, wherein the sequence thereof is SEQ ID NO: 3 or SEQ ID NO: 4.

Preferably, the nucleotide sequence encodes the fully human antibody specifically inhibiting Connexin 26 as described above.

The present invention also provides use of the fully human antibody specifically inhibiting Connexin 26 or the genetically engineered antibody in the manufacture of a medicament or kit for the treatment of deafness, skin disease or tumor caused by Connexin 26 mutation.

The present invention also provides a medicament for treating deafness, skin disease or tumor, wherein the medicament comprises the fully human antibody specifically inhibiting Connexin 26 or the genetically engineered antibody as an active ingredient.

The fully human antibody specifically inhibiting Connexin 26 of the present invention is named as Anti-Cx26-scFvII-Fc. Results show that the single chain antibody obtained by rounds of phage library screening can selectively bind to connexins and specifically inhibit hemichannel formed by the connexins. Anti-Cx26-scFvII-Fc is a recombinant single chain human antibody, which is different from the common IgG antibodies in clinical application. Anti-Cx26-scFvII-Fc has different antibody structure, biochemical characteristics and biological functions from IgG. Our experiments demonstrated that the Anti-Cx26-scFvII-Fc single chain antibody has a molecular weight of about 100 kd, recognizes and binds to the target antigen epitope of the connexin extracellular domain, specifically recognizes cells over-expressing connexin 26, and the antibody and connexin 26 are co-localized on the cell surface. Functional experiments show that Anti-Cx26-scFvII-Fc can inhibit the activity of the Connexin 26 hemichannel. Immunohistochemically staining of this antibody alone can more accurately diagnose the expression of human Connexin 26 in various tissues. In summary, the Anti-Cx26-scFvII-Fc single chain antibody has potential applications in the treatment of deafness, skin diseases and tumors, and Connexin 26 diagnostic reagents.

The present invention uses the 41-56 amino acid sequence of human Connexin 26 extracellular region as antigen, the amino acid sequence thereof is KEVWGDEQADFVCNTL (SEQ ID NO: 5). The antibody is obtained by single-chain antibody phage display library and screening technology. Through the biochemical analysis and immunofluorescence identification, it was confirmed that the antibody provided by the present invention specifically recognize connexin 26 and inhibit its formation of hemichannel activity. Animal experiments show that the antibody has a significant inhibitory effect on the hemichannel activity of mouse cochlear tissue sections. Therefore, the antibody can be used in the treatment of connexin-associated diseases.

BRIEF DESCRIPTION OF THE DRAWINGS

FIG. 1A shows results of Phage ELISA used to detect antigen-binding activity after enriching the antibody;

FIG. 1B shows results of ELISA assay of the binding between selected monoclonal antibody and antigen.

FIG. 2A shows structure diagram of scFv-Fc immunoglobulin;

FIG. 2B shows the molecular weight of the single chain antibody is about 58 KDa tested by western blot;

FIG. 2C shows results of the scFv II-Fc antibody thermal stability test;

FIG. 2D shows Mass Spectrometry show that the Anti-Cx26-scFv II-Fc dimer has a molecular weight of 105140.3

FIG. 3A shows results of the ELISA to test the antibody/Cx26 protein binding affinity;

FIG. 3B shows results of the SRP assay to test the antibody/Cx26 protein binding affinity (results showed that the anti-Cx26-scFv II-Fc antibody binding to Cx26 protein with a KD of 7.3E10-8M).

DETAILED DESCRIPTION OF THE EMBODIMENTS

Figure 1A:
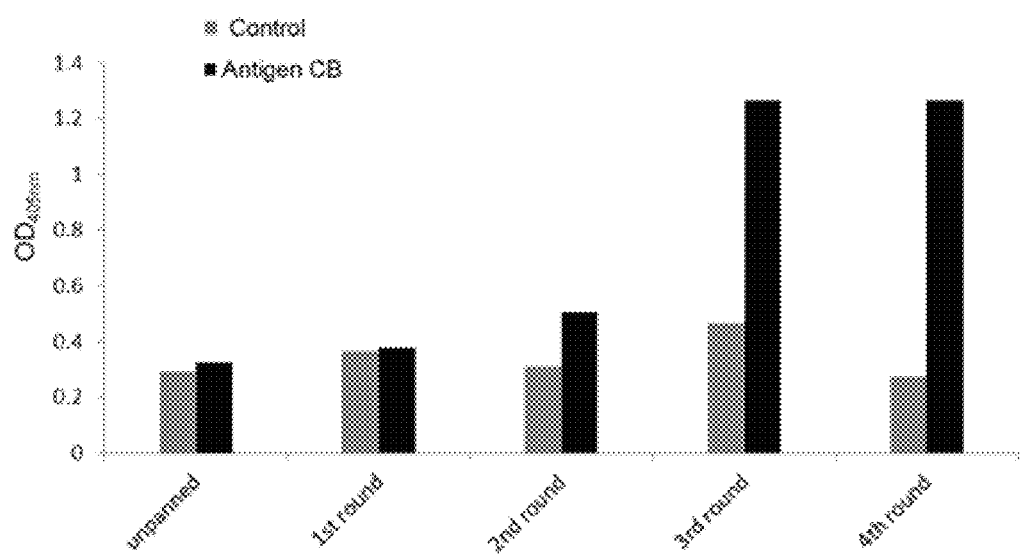
FIGS. 1A-1B show results of screening of single-chain antibody and sequence verification.

The present invention is further described below with reference to specific embodiments. It should be understood that these examples are only for illustrating the present invention and are not intended to limit the scope of the present invention. In addition, it should be understood that after reading of the present invention, those skilled in the art can make various modifications or changes to the present invention, and these equivalent forms also fall within the scope of the appended claims of the present application.

Example 1. Screening and Purification of the Single-Chain Antibody

1. Materials:
(1) biotinylated antigen polypeptide (sequence: KEVWGDEQADFVCNTL, SEQ ID NO: 5, hereinafter referred to as antigen) synthesized from Genscript. (2) laboratory's phage display human antibody library. (3) streptavidin magnetic beads purchased from Thermo Scientific. (4) high adsorption ELISA microplate purchased from Corning Corporation. (5) Anti-M13 HRP antibody purchased from Thermo Scientific. (6) Helper phage purchased from Life Technologies (Cat. No. 18311019). (7) XL1-Blue bacteria available from Agilent Technologies (Cat. NO. 200228). (8) developing solution ABTS solution purchased from Thermo Scientific, Cat. NO. 002024.

2. Method:
200 microliters of the phage display human antibody library expressing human single chain antibodies (containing $1\times10^{11}$ phage particles) was mixed with 5 micrograms of antigen, incubated at room temperature for 30 minutes and then added to 50 microliters of the streptavidin magnetic beads. Phages bound to the antigen was captured by the streptavidin magnetic beads, the unbound phage was removed by PBST rinsing, and then the stably bound phages was eluted with glycine-HCl (pH 2.2) buffer. XL1-Blue bacteria (Agilent Technologies Cat. No. 200228) was inoculated into 200 mL of SB medium and when the OD reached 0.6, the eluted phages were added to the XL1-Blue bacteria, and incubated at 37° C. for 30 minutes, and then incubated overnight at 30° C. The bacteria were collected by centrifugation and added with 30 microliters of helper phage (containing $1\times10^{11}$ helper phage particles). The next round of screening was performed after amplification. The above panning steps were repeated for 3-4 rounds. Then the phage-containing XL1-Blue broth was thoroughly diluted and plated onto 10 cm plates with 100-500 clones on each plate, and monoclones were picked. The phage ELISA test was carried out after each round of phage library panning.

The phage ELISA test comprises the following steps: inoculating the phage-containing XL1-Blue monoclonal bacteria into 200 microliters of SB medium in a 96 well plate, shaking at 37° C. with a speed of 200 rpm for 4-6 hours, adding 1 microliter helper phage when the OD is close to 0.6, and shaking at 30° C. overnight, centrifuging the next day to collect the supernatant at 3000 g for use, coating a 96 low-permeability microplate with the antigen overnight, adding the prepared phage in the supernatant to the microplate, incubating for 2 hours at room temperature, then adding the Anti-M13 HRP antibody and incubating for 30 minutes, washing for three times with PBST, and adding 50 microliter of ABTS as developing solution.

The result of the enzyme-linked immunosorbent assay (ELISA) shows that, as panning proceeds, the signal of the enzyme-linked immunosorbent rises continuously while the signal of the control antigen (Acro Biosystems, catalog number CDO-H82F2) is still low. After the fourth round panning, the signal intensity of the antigen was multiple times of that of the control antigen, indicating that after 4 rounds of panning, the phages capable of expressing the antigen-specific binding antibody were enriched. Monoclony was picked from the library of the third and fourth round, and the clone with ELISA results more than double of that of the control clone was selected as a positive clone. The sequence of the positive clone was analyzed, and different antibody sequences and enrichment situations were determined by comparison analysis.

Figure 1B:
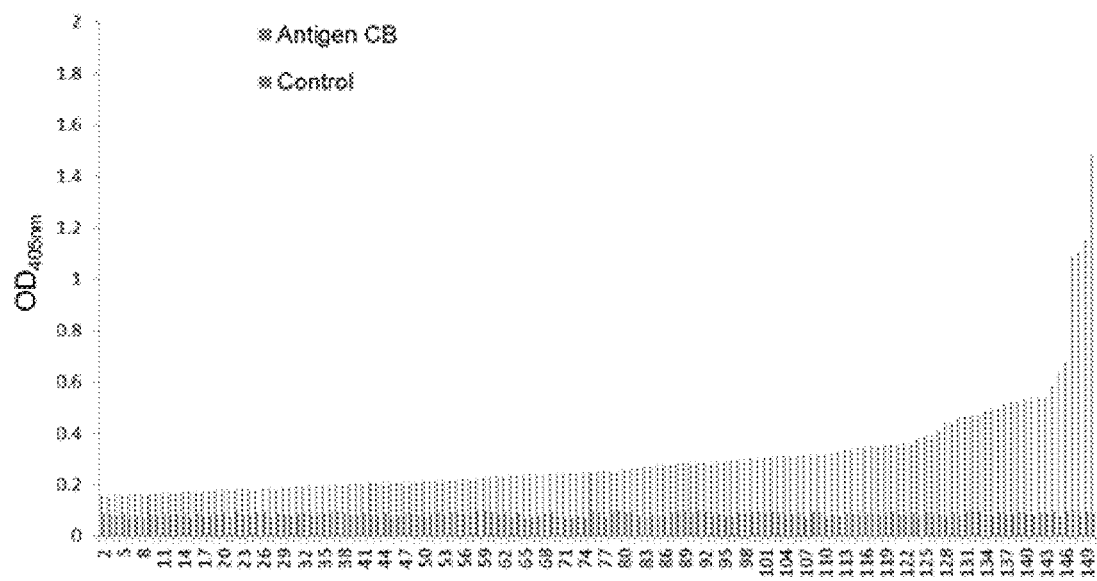

3. Results:
As shown in FIG. 1A, the peptide antigen CB was screened against the phage display human antibody library. After 4 rounds of selection, the ELISA readout of the selected group was continuously increased compared with the control group. 700 monoclonal antibodies were picked and tested by ELISA assay, and the clone with ELISA results more than double of that of the control group was selected as positive clone, as shown in FIG. 1B. Sequencing analysis of 150 positive clones was carried out. After comparison and alignment analysis, the effective enrichment sequence was determined based on that those with higher repeats have the stronger binding affinity of the antibody. The positive clone selected in the present invention were repeated 84 times in the 150 clone sequences, thus has a high affinity.

The selected positive clone was sequenced and the nucleic acid sequence of the selected positive clone was SEQ ID NO: 3.

Example 2. Single-Chain Antibody Purification and Biochemical Properties Detection 1. Materials:
(1) Sypro Orange dyes were purchased from Thermo Scientific. (2) pFUSE expression vector pFUSE-hIGg1-FC2 was purchased from Invivogen Company, catalog No. pfuse-hglfc2. (3) HiTrap Protein A HP columns were purchased from GE. (4) ÄKTApurifier100 protein purifier was purchased from GE. (5) Real-time quantitativePCR instrument was purchased from BioRad company. (6) Plasmid extraction kit was purchased from Qiagen company. (7) BCA Protein Assay Kit (Pierce™ BCA Protein Assay kit, Pierce #23253). (8) BamH1 and BglII restriction enzymes were purchased from NEB.

2. Methods:
The positive sequence obtained in Example 1 (i.e., SEQ ID NO: 3) was synthesized by gene synthesis method (Nanjing GenScript Ltd.) and added with the restriction sites BamH1 and BglII at both ends of the sequence. The obtained nucleic acid sequence was inserted into the pFUSE-hIGg1-FC2 expression vector (Invivogen Corporation, with reference to the procedures described in the instruction manual)

after enzyme digestion at the restriction sites BamH1 and BglII with reference to the procedures described in the instruction manual of NEB to obtain an eukaryotic antibody expression plasmid of Anti-Cx26-scFvII-Fc, which is a single chain antibody having an Fc segment. 293Fectin reagent (Invitrogen Corporation, Cat. No. 12347500) was mixed with the eukaryotic antibody expression plasmid with a volume mass ratio of 30 microliter: 15 micrograms. The obtained mixture was added to 30 mL of 293 Freestyle suspension cells (available from Thermo Corporation) and incubated with shaking at 1200 rpm and 37° C. overnight. The supernatant was collected after centrifugation, and the antibody protein (Anti-Cx26-scFvII-Fc) was purified by using HiTrap Protein A HP columns on AKTA purifier 100 protein purifier. At last, the antibody concentration was tested by using the BCA Protein Assay Kit (Pierce, Cat #23252) with reference to the procedures described in the instruction manual.

The purified antibody was tested by Western blot: 5 micrograms of the purified antibody sample was loaded for SDS-PAGE electrophoresis, with electrophoresis voltage of 110V, 60 minutes, transferred to a cellulose acetate membrane, and then hybridized with horseradish peroxidase goat-anti-human secondary antibody (Thermo Scientific). The membrane was rinsed and then added with developing reagent (Pierce, Cat #35055) for imaging.

The purified antibody was subjected to heat stability test with the following steps: diluting the purified antibody to 0.1 mg/ml, adding Sypro Orange dye with a volume ratio of 1:2000 and sealing, loading onto the real-time quantitative PCR instrument (BioRad) with a heating program from 25° C. to 90° C., 0.5° C. per minute, and detecting fluorescence values.

The purified antibody was test on LC-MS mass spectrometry with the following steps: mixing 5 micrograms of the purified antibody with 1 microliter of PNGase enzyme (available from NEB Inc., Catalog No. P0709S) at 37° C. for one hour, and loading onto an Agilent 6230 TOF LC/MS instrument for high resolution mass spectrometry.

Figure 2A:
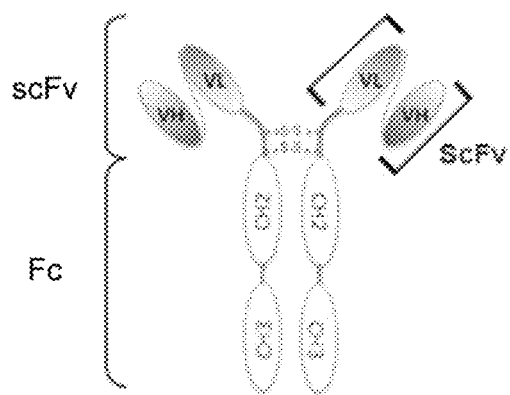
FIGS. 2A-2D show structure and biochemical activity identification of the single-chain antibody.

3. Results:

The nucleic acid sequence (SEQ ID NO: 3) obtained in Example 1 was inserted into the pFUSE-hIGg1-FC2 expression vector after enzyme digestion to obtain scFv II DNA sequence (SEQ ID NO: 4) containing the Fc region. The scFv II DNA sequence is capable of encoding a fully human single chain antibody (Anti-Cx26-scFvII-Fc, SEQ ID NO: 6) specifically inhibiting of Connexin 26, i.e., the fully human antibody specifically inhibiting Connexin 26, which is a recombinant immunoglobulin having the structure of scFv-Fc, shown in FIG. 2A, wherein scFv refers to a single-chain antibody comprising a heavy chain variable region and a light chain variable region, the amino acid sequence of the heavy chain variable region is SEQ ID NO: 1, the amino acid sequence of the light chain variable region is SEQ ID NO: 2, the sequence of the heavy chain CDR 3 region is DFSWRGYYMDV (amino acids 99-109 of SEQ ID NO: 1), the sequence of the light chain CDR3 region is QQYGSSPRT (amino acids 89-97 of SEQ ID NO: 2), and Fc refers to constant region. The constant region comprises a CH2 constant region and a CH3 constant region. The fully human antibody specifically inhibiting Connexin 26 specifically recognizes the 41-75 amino acid portion of the extracellular region of Connexin 26.

Figure 2B:
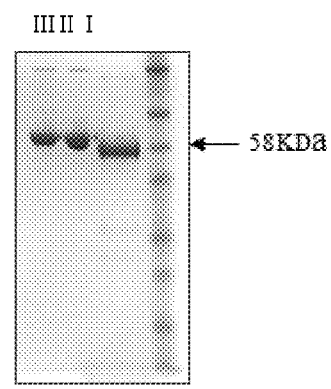
Figure 2C:
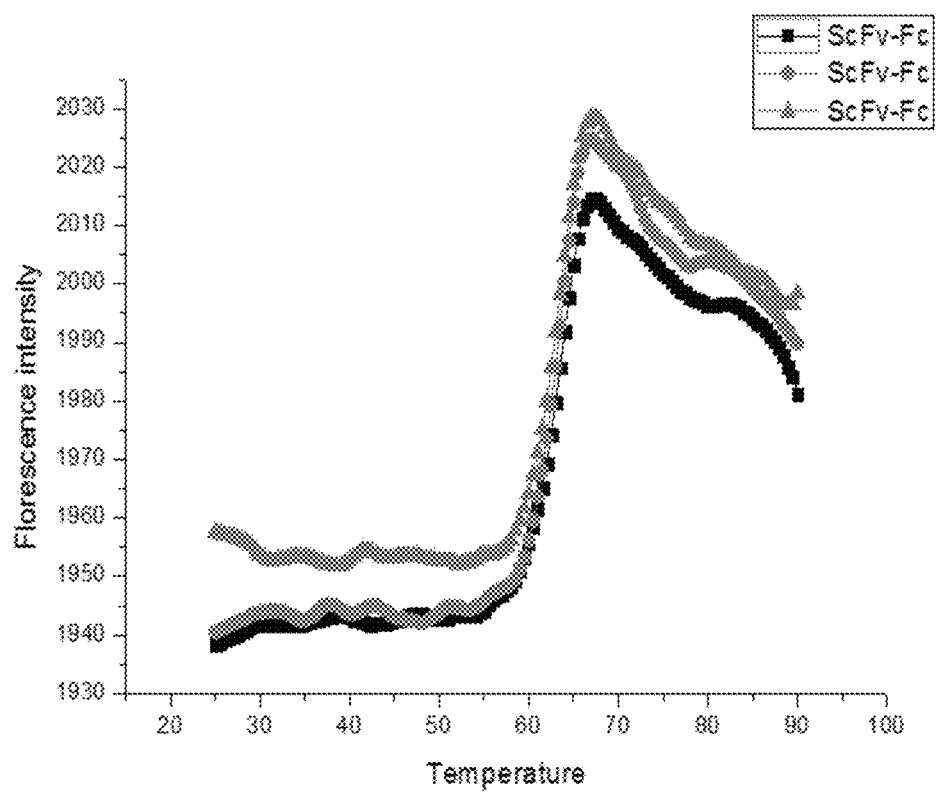
Figure 2D:
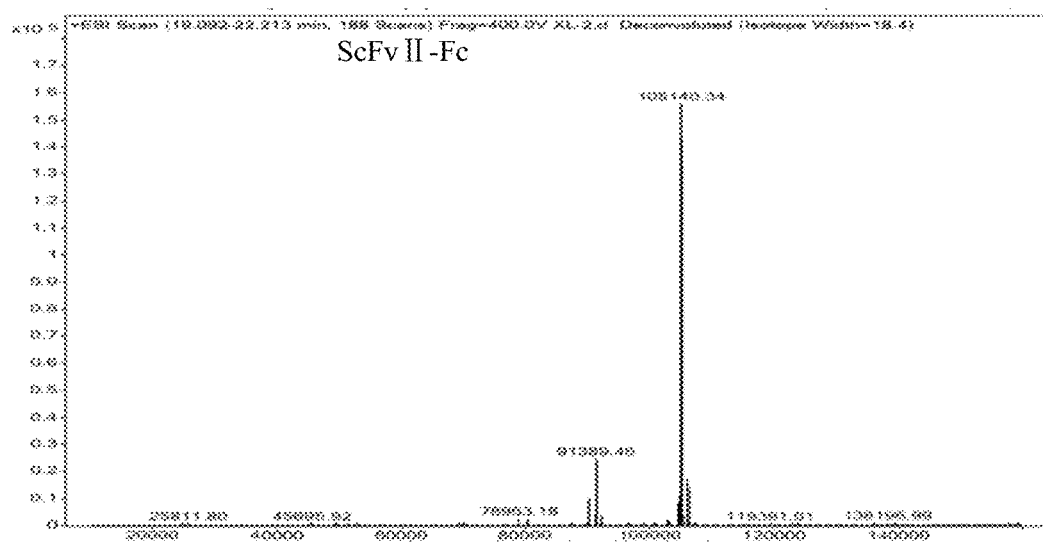

The Western blot result is shown in FIG. 2B. The obvious band at 58 kd shows that the antibody can specifically recognize Cx26 protein. The Tm of the antibody is 65° C. calculated by using the thermal stability test results, as shown in FIG. 2C, thus the described Anti-Cx26-scFv II-Fc antibody have high stability. The mass spectrometry results of LC-MS, shown in FIG. 2D, shows that the molecular weight of the antibody is 105140 Daltons.

Example 3. ELISA Assay to Test the Binding of the Single Chain Antibody to Connexin 26

1. Materials:

1. CBS antigen fixation solution was purchased from Thermo Scientific. 2. Anti-Human Fc HRP secondary antibody was purchased from Thermo Scientific. 3. Developing substrate ABST solution was purchased from ThermoScientific. 4. 96-well flat bottom plate was purchased from Corning Corporation.

2. Methods:

50 μl per well of the Cx26 polypeptide antigen (synthesized by GenScript, diluted with the CBS antigen fixation solution, SEQ ID NO: 5) and 0.05 μg per well of the antigen were added to the 96-wellplate, incubated overnight at 4° C., and then incubated with shaking at room temperature for 30 min. The 96-well plate was rinsed for three times with PBS, blocked with PBST solution containing 5% milk at 37° C. for 60 minutes and rinsed with PBS for three times. The Anti-Cx26-scFv II-Fc antibody obtained in Example 2 was added and incubated at 37° C. for 60 minutes. After the 96-wellplate was rinsed and dried, the anti-Human Fc secondary antibody was added thereto and incubated for 30 minutes with shaking at room temperature. The 96-well plate was rinsed for three times with PBS, added with the developing substrate and eventually read with a microplate reader.

Figure 3A:
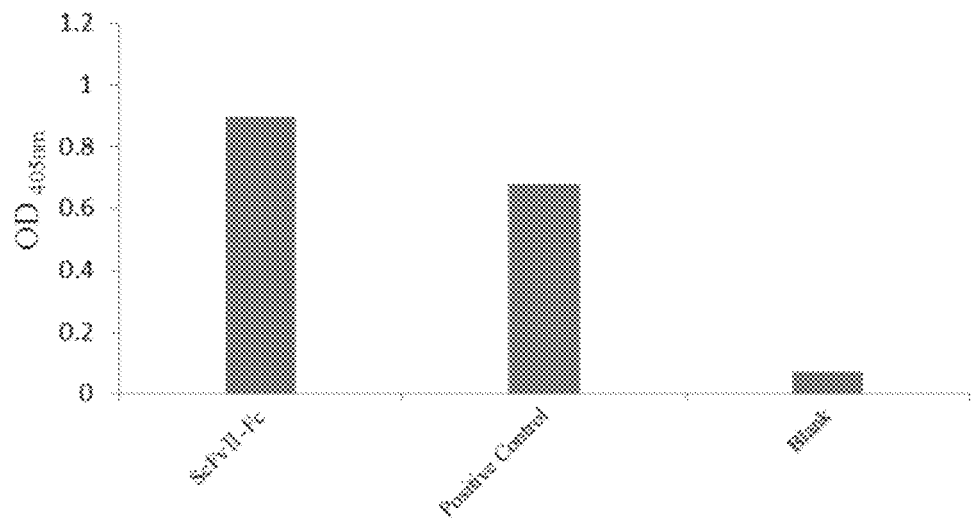
FIGS. 3A-3B show the test results of binding affinity between Anti-Cx26-scFv II-Fc antibody and Cx26 antigen.

3. Results:

As shown in FIG. 3A, the OD values of the negative control wells were less than 0.2 and the OD values of the positive wells were more than 0.4. Based on the ELISA results, 150 positive colonies wells were selected.

Example 4. Detection of the Combination of the Single Chain Antibody and Connexin 26 by SRP 1. Materials:

1. Octet RED instrument and its detection chip (CM5 chip) was purchased from Pall Corporation. 2. Anti-human IgG antibody was purchased from Thermo Scientific.

2. Experimental Method:

The affinity and kinetics of the antibody and the antigen were detected by the method of multi cycle kinetics. Immobilization of the antibody was performed by capture method. First, the anti-human IgG antibody was coupled to the CM5 chip, and then the Anti-Cx26-scFv II-Fc antibody sample flowed through the chip surface after being serial diluted. The antibody to be detected was then captured by the coupled anti-human Fc antibody. Then the polypeptide antigen (synthesized by Nanjing Genscript Co. Ltd, sequence: SEQ ID NO: 5) was added, the antigen was bound with the antibody, and the signal was detected and recorded. Finally, the antibody and the antigen samples on the CM5 chip surface were eluted by regeneration reagent (glycine solution, pH1.7) for a new round of testing.

Figure 3B:
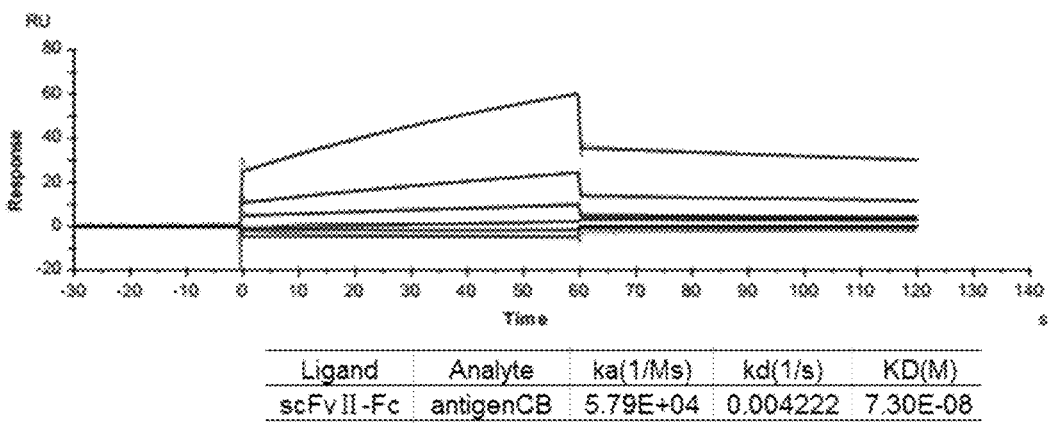

3. Results:

As shown in FIG. 3B, the SRP detection of the interaction between the antibody and connexin 26 showed that the resulting KD of Anti-Cx26-scFv II-Fc antibody with Cx26 was 7.3E10-8 M.

Example 5. Cellular Immunofluorescence Detection of Cx26 Protein Specifically Recognized by the Antibody 1. Materials:

(1) HeLa DH cells were purchased from Sigma company. (2) Cx26-Venus-YFP reporter plasmid was purchased from Addgene, Cat. No. 69016. (3) Fluorescent secondary antibody Alexa Fluor 594 goat anti-human was purchased from Thermo Scientific. (4) Fluorescence confocal microscope was purchased from Leica company.

2. Methods:

Cx26-Venus-YFP plasmid was transfected into HeLa DH cells with 293Fectin (Thermo) with reference to the procedures described in the instruction manual. The plasmid Cx26-Venus-YFP can express human Cx26 protein on the cell membrane with green fluorescence. After fixed with 2% formalin, the cells kept at room temperature for 10 minutes. After rinsed, the cells were blocked with 2% BSA in PBS for 30 min, and then incubated for 4 to 5 hours in the Anti-Cx26-scFvII-Fc antibody solution, which was obtained by diluting 1 mg/mL Anti-Cx26-scFvII-Fc antibody solution with 1% BSA/PBS with a dilution ratio of 1:500. After rinsed, the cells were added with the fluorescent Alexa Fluor 594 goat anti-human secondary antibody, which was diluted in 1% BSA/PBS solution with a dilution ratio of 1:1000. The cells were incubated at room temperature for 60 min, added with DAPI (1 μg/mL) and incubated for 5 minutes, rinsed, mounted on a confocal laser scanning microscope, and detected.

Figure 4:
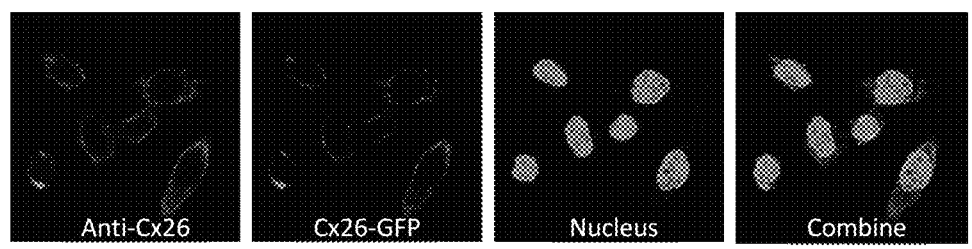
FIG. 4 shows results of the immunofluorescence test of Anti-Cx26-scFv II-Fc antibody and Cx26-GFP protein for co-localization (results showed that these two proteins co-localized).

3. Results:

As shown in FIG. 4, the Anti-Cx26-scFv II-Fc antibody co-localized with both Cx26-GFP proteins.

Example 6. Patch Clamp Technique Detection of Cx26 Hemichannel Activity Inhibited by the Antibody 1. Materials:

(1) HeLa DH cells were purchased from Sigma company. (2) Cx26-Venus-YFP reporter plasmid was purchased from Addgene, Cat. No. 69016. (3) Automatic patch clamp system was purchased from the United States MDC company.

2. Methods:

Cx26-Venus-YFP plasmid was transfected into HeLa DH cells with 293Fectin (Thermo) with reference to the procedures described in the instruction manual. Whole cell patch clamp was used to record the single membrane ion currents. 940 nM Anti-Cx26-scFv II-Fc antibody was added into the supernatant of the cells, while 100 uM $Zn^{2+}$ was added in a positive control group and no antibody was added in a blank control group. The voltage was increased to 40 millivolts so that the cells were depolarized, which led to the opening of Cx26 hemichannel. The hemichannel currents of the experimental group added with the antibody, the positive control group and the blank control group were recorded. The voltage was decreased to minus 40 millivolts to hyperpolarize the cells and simultaneously recorded the hemichannel current in each group.

Figure 5:
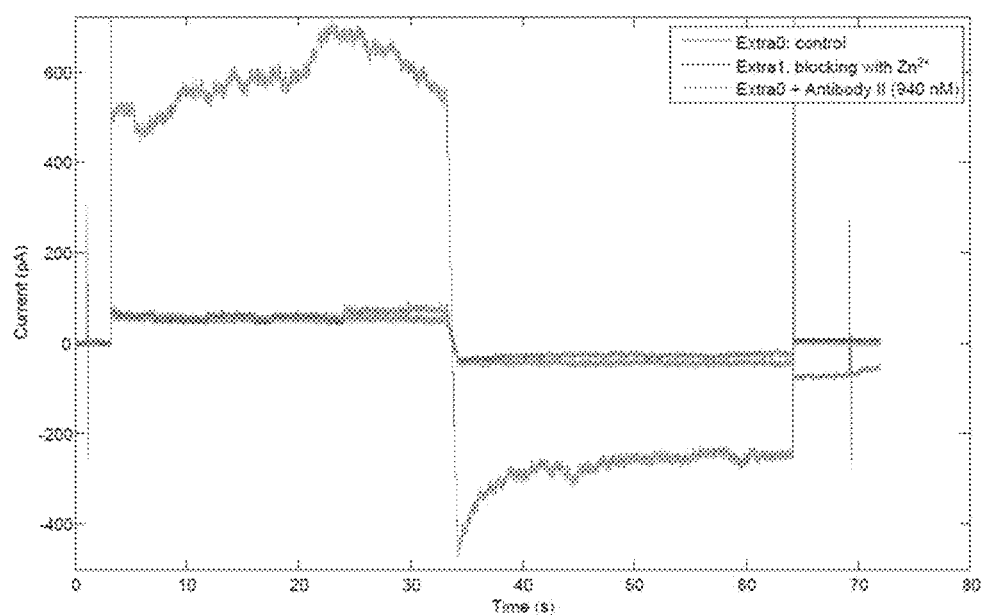
FIG. 5 shows that Anti-Cx26-scFv II-Fc antibodies block the Cx26 hemichannel activity testing by patch-clamp techniques after depolarization activated Cx26 ion channels.

3. Results:

As shown in FIG. 5, the antibody Anti-Cx26-scFv II-Fc can effectively inhibit Cx26 hemichannel activity, which is 100 folds higher than the non-specific inhibitor $Zn^{2+}$.

What is claimed is:

1. An antibody or antigen binding fragment thereof that specifically inhibits Connexin 26, wherein the antibody or the antigen binding fragment comprises a heavy chain variable region ($V_H$) and a light chain variable region ($V_L$), wherein the $V_H$ comprises the $V_H$-CDR1-3 sequences set forth in SEQ ID NO: 6, and wherein the $V_L$ comprises the $V_L$-CDR1-3 sequences set forth in SEQ ID NO: 6.

2. A medicament comprising a pharmaceutic acceptable carrier and the antibody or the antigen binding fragment according to claim 1.

3. The antibody or the antigen binding fragment of claim 1, wherein the antigen binding fragment is a Fab, F(ab)', Fd, sc$F_v$, or $F_v$.

4. The antibody or the antigen binding fragment of claim 1, wherein the $V_H$ comprises the amino acid sequence of SEQ ID NO: 1 and the $V_L$ comprises the amino acid sequence of SEQ ID NO: 2.

5. The antibody or the antigen binding fragment of claim 4, wherein the antigen binding fragment is a scFv-Fc.

6. The antibody or the antigen binding fragment of claim 5, wherein the scFv-Fc comprises the amino acid sequence of SEQ ID NO: 6.

7. A method for inhibiting hemichannel activity of Connexin 26 in a subject in need thereof comprising administering the antibody composition of claim 1 to the subject in an amount sufficient to inhibit hemichannel activity of Connexin 26.

8. The method of claim 7, wherein the subject comprises a mutation in Connexin 26.

9. The method of claim 8, wherein the mutation in Connexin 26 causes aberrant hemichannel opening or closing.

10. The method of claim 8, wherein the mutation in Connexin 26 is associated with deafness or skin disease.

* * * * *

SEQUENCE LISTING

```
<160> NUMBER OF SEQ ID NOS: 6

<210> SEQ ID NO 1
<211> LENGTH: 122
<212> TYPE: PRT
<213> ORGANISM: Homo sapiens

<400> SEQUENCE: 1

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser His Gly Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Trp Arg Gly Tyr Tyr Met Asp Val Trp Gly Lys
            100                 105                 110

Gly Thr Leu Val Thr Val Ser Ser Gly Ser
        115                 120

<210> SEQ ID NO 2
<211> LENGTH: 108
<212> TYPE: PRT
```

<213> ORGANISM: Homo sapiens

<400> SEQUENCE: 2

```
Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gly Gly Thr Lys Val Glu Ile Lys Arg
            100                 105
```

<210> SEQ ID NO 3
<211> LENGTH: 732
<212> TYPE: DNA
<213> ORGANISM: Artificial Sequence
<220> FEATURE:
<223> OTHER INFORMATION: Sequence of the selected positive clone of the single chain antibody

<400> SEQUENCE: 3

```
caggtacagc tgcagcagtc aggggggggc gtggtccagc ctggggaggtc cctgagactc        60
tcctgtgcag cctctggatt caccttcagt agctatgcta tgcactgggt ccgccaggct       120
ccaggcaagg ggctggagtg ggtggcagtt atatcacatg gtggaagtaa taaatactac       180
gcagactccg tgaagggccg attcaccatc tccagagaca attccaagaa cacgctgtat       240
ctgcaaatga acagcctgag agctgaggac acggctgtgt attactgtgc gagagatttt       300
agttggagag ggtactacat ggacgtctgg ggcaaaggca ccctggtcac cgtctcctca       360
ggcagcggcg gtggcggatc cgaaacgaca ctcacgcagt ctccagccac cctgtctttg       420
tctccagggg aaagagccac cctctcctgc agggccagtc agagtattag cagctactta       480
gcctggtacc agcagaaacc tggccaggct cccaggctcc tcatctatgg tgcatccacc       540
agggccactg gcatcccaga caggttcagt ggcagtgggt ctgggacaga cttcactctc       600
accatcagca gactggagcc tgaagatttt gcagtgtatt actgtcagca gtatggtagc       660
tcacctcgaa ctttcggcgg agggaccaag gtggaaatca acgtggcct cgggggccat        720
atcggccatg gt                                                          732
```

<210> SEQ ID NO 4
<211> LENGTH: 1416
<212> TYPE: DNA
<213> ORGANISM: Artificial Sequence
<220> FEATURE:
<223> OTHER INFORMATION: scFv II DNA sequence containing the Fc region

<400> SEQUENCE: 4

```
caggtacagc tgcagcagtc aggggggggc gtggtccagc ctggggaggtc cctgagactc        60
tcctgtgcag cctctggatt caccttcagt agctatgcta tgcactgggt ccgccaggct       120
ccaggcaagg ggctggagtg ggtggcagtt atatcacatg gtggaagtaa taaatactac       180
gcagactccg tgaagggccg attcaccatc tccagagaca attccaagaa cacgctgtat       240
```

```
ctgcaaatga acagcctgag agctgaggac acggctgtgt attactgtgc gagagatttt    300
agttggagag ggtactacat ggacgtctgg ggcaaaggca ccctggtcac cgtctcctca    360
ggcagcggcg gtggcggatc cgaaacgaca ctcacgcagt ctccagccac cctgtctttg    420
tctccagggg aaagagccac cctctcctgc agggccagtc agagtattag cagctactta    480
gcctggtacc agcagaaacc tggccaggct cccaggctcc tcatctatgg tgcatccacc    540
agggccactg gcatcccaga caggttcagt ggcagtgggt ctgggacaga cttcactctc    600
accatcagca gactggagcc tgaagatttt gcagtgtatt actgtcagca gtatggtagc    660
tcacctcgaa ctttcggcgg agggaccaag gtggaaatca acgtggcct cgggggcccc     720 atggttagat ctgacaaaac tcacacatgc ccaccgtgcc cagcacctga actcctgggg    780
ggaccgtcag tcttcctctt ccccccaaaa cccaaggaca cctcatgat ctcccggacc      840 cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagcc ccgagaacca caggtgtaca ccctgccccc atcccgggag     1140
gagatgacca gaaccaggt cagcctgacc tgcctggtca aaggcttcta tcccagcgac     1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcacg aggctctgca caaccactac    1380
acgcagaaga gcctctccct gtctccgggt aaatga                               1416

<210> SEQ ID NO 5
<211> LENGTH: 16
<212> TYPE: PRT
<213> ORGANISM: Artificial Sequence
<220> FEATURE:
<223> OTHER INFORMATION: Antigen polypeptide

<400> SEQUENCE: 5

Lys Glu Val Trp Gly Asp Glu Gln Ala Asp Phe Val Cys Asn Thr Leu
1               5                   10                  15

<210> SEQ ID NO 6
<211> LENGTH: 471
<212> TYPE: PRT
<213> ORGANISM: Artificial Sequence
<220> FEATURE:
<223> OTHER INFORMATION: Fully human single chain antibody (Anti-Cx26-
      scFv II-Fc)

<400> SEQUENCE: 6

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser His Gly Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95
Ala Arg Asp Phe Ser Trp Arg Gly Tyr Tyr Met Asp Val Trp Gly Lys
            100                 105                 110
Gly Thr Leu Val Thr Val Ser Ser Gly Ser Gly Gly Gly Ser Glu
        115                 120                 125
Thr Thr Leu Thr Gln Ser Pro Ala Thr Leu Ser Leu Ser Pro Gly Glu
        130                 135                 140
Arg Ala Thr Leu Ser Cys Arg Ala Ser Gln Ser Ile Ser Ser Tyr Leu
145                 150                 155                 160
Ala Trp Tyr Gln Gln Lys Pro Gly Gln Ala Pro Arg Leu Leu Ile Tyr
                165                 170                 175
Gly Ala Ser Thr Arg Ala Thr Gly Ile Pro Asp Arg Phe Ser Gly Ser
            180                 185                 190
Gly Ser Gly Thr Asp Phe Thr Leu Thr Ile Ser Arg Leu Glu Pro Glu
        195                 200                 205
Asp Phe Ala Val Tyr Tyr Cys Gln Gln Tyr Gly Ser Ser Pro Arg Thr
    210                 215                 220
Phe Gly Gly Gly Thr Lys Val Glu Ile Lys Arg Gly Leu Gly Gly Pro
225                 230                 235                 240
Met Val Arg Ser Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470
```